United States Patent [19]
Faccioli et al.

[11] Patent Number: 5,435,645
[45] Date of Patent: * Jul. 25, 1995

[54] PROCESS AND APPARATUS FOR THE MIXING AND DIRECT EMPLACEMENT OF A TWO-COMPONENT BONE CEMENT

[75] Inventors: Giovanni Faccioli, Montova; Renzo Soffiatti, Verona, both of Italy

[73] Assignee: Tecres SpA, Verona, Italy

[ * ] Notice: The portion of the term of this patent subsequent to Mar. 16, 2010 has been disclaimed.

[21] Appl. No.: 915,434

[22] Filed: Jul. 17, 1992

Related U.S. Application Data

[63] Continuation-in-part of Ser. No. 621,847, Dec. 4, 1990, Pat. No. 5,193,907.

[30] Foreign Application Priority Data

Dec. 29, 1989 [IT] Italy ......................... 85010

[51] Int. Cl.[6] .................... B01F 15/02; B65D 1/04
[52] U.S. Cl. .................... 366/130; 222/386; 366/139; 366/184; 366/256; 604/87
[58] Field of Search ............... 366/130, 139, 129, 191, 366/184, 255, 150, 154, 256; 222/137, 145, 386; 604/82-87

[56] References Cited

U.S. PATENT DOCUMENTS

| | | | |
|---|---|---|---|
| 3,595,439 | 7/1971 | Newby | 604/87 |
| 4,676,655 | 6/1987 | Handler | 366/130 |
| 4,983,164 | 1/1991 | Hook | 604/87 |
| 5,015,101 | 5/1991 | Draenert | 366/130 |

FOREIGN PATENT DOCUMENTS

| | | |
|---|---|---|
| 0242956 | 10/1987 | European Pat. Off. . |
| 0380867 | 8/1990 | European Pat. Off. . |
| 2801706 | 3/1980 | Germany . |
| 1314234 | 4/1973 | United Kingdom . |
| 2193654 | 2/1988 | United Kingdom . |
| 8504567 | 10/1985 | WIPO . |
| 85504567 | 10/1985 | WIPO . |
| 8606618 | 11/1986 | WIPO . |
| 8705492 | 9/1987 | WIPO . |
| 8803811 | 6/1988 | WIPO . |
| 8802265 | 7/1988 | WIPO . |

*Primary Examiner*—Robert W. Jenkins
*Attorney, Agent, or Firm*—Ladas & Parry

[57] ABSTRACT

A process and apparatus is disclosed for the mixing and direct emplacement of a bone cement formed from two components, one liquid and one powder, comprising the steps of storing the two components separately in a multichamber container, opening the liquid phase container within one of the said chambers which is not in communication with the outside atmosphere, setting up a negative pressure within the chamber containing the powder phase, causing aspiration of the liquid into the chamber containing the powder, mixing the two phases, compacting the paste obtained, injecting the paste into a cannula and extruding the paste with direct emplacement of the cement.

18 Claims, 9 Drawing Sheets

PROCESS AND APPARATUS FOR THE MIXING AND DIRECT EMPLACEMENT OF A TWO-COMPONENT BONE CEMENT

CROSS-REFERENCE TO RELATED APPLICATIONS

This application is a continuation-in-part of application Ser. No. 07/621,847, filed Dec. 4, 1990 now Pat. No. 5,193,907.

The present invention relates to a process for the mixing and direct emplacement of a bone cement formed from two components, one liquid and one powder, which components are kept separate until the cement is required for use, each component comprising a mixture of one or more mutually compatable components, and to apparatus for carrying out such process.

Currently known systems for the preparation of bone cement include at least one stage during which the liquid component, which is predominantly based on a monomer, is able to disperse its highly toxic vapours into the environment. These vapours can then be inhaled by the operator handling the cement during this stage with a consequential serious hazard to the operators health if this operation is performed frequently.

In most cases, the components of a bone cement are stored prior to use in two different containers, such as for example sachets of plastics material for the powder component and glass vials for the liquid component. Because of the very high reactivity of the liquid component, and its toxicity, its container must have special mechanical strength properties and be resistant to chemical attach by the liquid contained therein.

When preparing the cement paste, the operator opens the vial and pours the liquid into a container into which the powder component has previously been placed, or vice versa. The operator then mixes the two components with a spatula, or places a cover fitted with an externally operable rotatory spatula on the container.

In both cases, vapour from the liquid component is left free to diffuse, and this can be inhaled by persons in its immediate vicinity.

Known mixing systems also have a further disadvantage associated with the fact that certain operations bring components of the cement mixture into contact with the environmental atmosphere, in such a way that germs present in the air can contaminate the components and can subsequently infect the bone of the patient operated on when the cement is in position.

An object of the invention is to provide a method for the preparation and direct emplacement of a bone cement formed from a solid and a liquid component which is simple and practical, which requires no fixed equipment, such as suction hoods or centrifuging equipment, which provides a perfectly aseptic bone cement, which is homogeneous and has minimum porosity, and which avoids releasing the toxic vapours of the liquid component into the environment.

According to the present invention there is provided a process for mixing a bone cement formed from two components, one liquid and one powder, which components are kept separate until the cement is required for use, each component comprising a mixture of one or more components which are mutually compatible, and if required, for delivering it directly in situ, such process comprising the following steps:

separately storing the two components which are to be mixed, within a container comprising a plurality of chambers aseptically isolated from the outside atmosphere;

opening the container for the liquid component within one of the aforesaid chambers which does not communicate with the outside atmosphere;

creating a negative pressure in the chamber containing the powder component;

said negative pressure causing suction of the liquid component into the chamber containing the powder component, the two chambers being kept isolated from the outside atmosphere.

mixing the two components by agitation of the container;

compacting the cement paste obtained by compressing same;

inserting, if required, a flexible cannula so as to direct the outflow of paste; and extruding the paste by manual or mechanical or pneumatic action on a plunger, causing direct in situ emplacement of the cement.

Also according to the present invention there is provided an apparatus for carrying out such process, said apparatus comprising a substantially cylindrical hollow body, a cover which can be attached to the said body, said cover having an aperture or holecoaxial with the longitudinal axis of the body and a plunger consisting of a stem which can move axially inside the said hole and a head which together with body bounds the chamber which aseptically houses the powder component of the cement, in which said body has at its base and projecting outwardly a hollow cylindrical needle which can be closed off by means of a sealing plug and in which the plunger which can move within the cylindrical cavity of the said body has a cavity forming the chamber housing the container of the liquid component of the cement, fitted with means for breaking the container which can be operated from outside the chamber itself and in which the chamber housing the powder component and the chamber housing the container of the liquid component are placed by means of a plurality of holes protected by a filter and located on the said head.

A first advantage of this invention derives from the fact that the process allows the two liquid and powder components of the bone cement to be mixed without hazardous inhalation of the toxic vapours of the liquid component by those present.

A second advantage derives from the fact that with the process according to the invention the paste is never directly handled by the operator and always remains in an isolated aseptic environment before and during direct emplacement, and therefore the paste cannot be contaminated by germs present in the ambient air and in the operating theatre.

Another advantage derives from the reduced porosity of the cement obtained with the process according to the invention. This reduced porosity also results in an improvement in the mechanical strength properties of the cement, in addition to improved homogeneity of the paste.

A further advantage derives from the special simplicity and practicality in use of the apparatus for implementing the process according to the invention, and the possibility of constructing this apparatus with materials which permit single use. This apparatus therefore is appropriate for use in environments which are not very congenial, such as for example field hospitals or any other environments not provided with aseptic air.

The present invention will be further illustrated, by way of example, with reference to the accompanying drawings, in which.

The process for the mixing and direct emplacement of a bone cement formed from two components, one liquid and one powder, which are kept separate until the cement is ready for use includes the following steps:

separate storage of the two components within a single container consisting of a plurality of intercommunicating chambers, but aseptically isolated from the outside atmosphere, opening of the container for the liquid component within one of the said chambers, out of direct communication with the outside air, the creation of a negative pressure within the chamber containing the powder component, suction of the liquid component, by suction due to the said negative pressure, into the chamber containing the powder component, the two chambers being kept isolated from the outside air, mixing of the two components by agitation of the container, compaction of the cement paste so obtained by compression thereof with possible further aspiration of air by means of a vacuum-producing installation, the possibility of fitting of a cannula in order that the emerging paste may be better directed, extrusion of the paste by manual or mechanical or pneumatic action on a plunger, and direct in situ emplacement of the cement.

Figure 1:
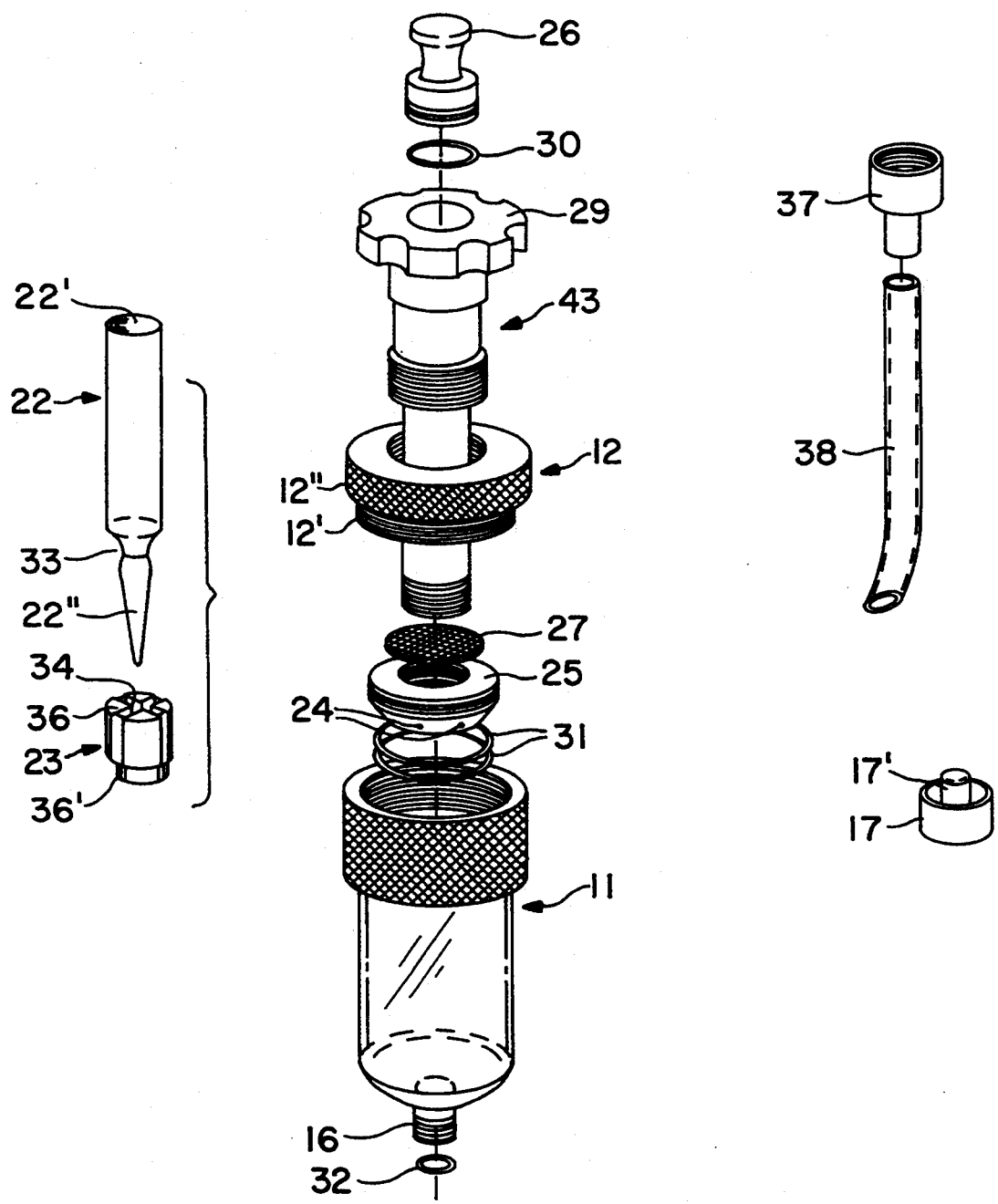
FIG. 1 is a diagrammatic exploded view, in partial cross-section of apparatus according to the invention.
Figure 2:
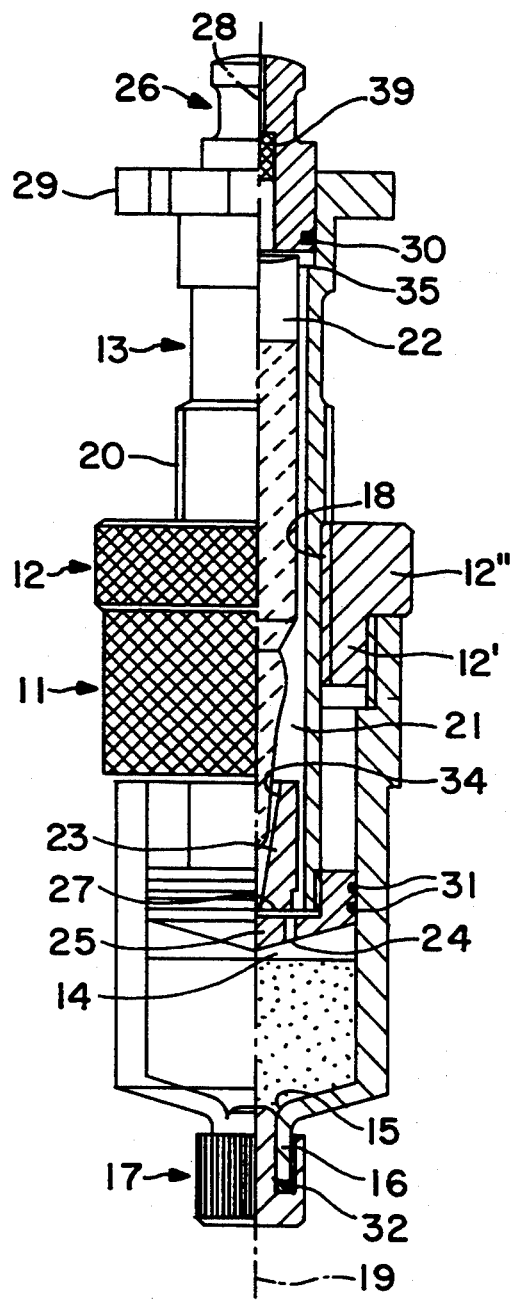
FIG. 2 is an imploded view, in partial cross-section, of the apparatus in FIG. 1 when ready for use.

Bearing in mind that identical reference numerals correspond to identical or equivalent parts in the drawings, with reference to FIGS. 1 and 2 it will be noted that the apparatus for implementing the process according to the invention comprises a substantially cylindrical hollow body 11, a cover 12 and a plunger 13 which can mover axially between chamber 14 consisting of the cylindrical cavity formed in said body 11 and cover 12.

The longitudinal axis of the said cylindrical cavity coincides with the longitudinal axis 19 of the entire apparatus. Body 11 has a hollow cylindrical needle 16 fitted with a sealing plug 17 projecting outwardly from the base of the said cavity.

Cover 12 has a lower part 12' which can be screwed between the said body and an upper cylindrically shaped externally knurled part 12" having an external diameter which is slightly greater than the external diameter of body 11.

The said cover also has a threaded hole 18 coaxial with said longitudinal axis 19, within which stem 20 of plunger 13 can move axially so that its central threaded portion can be screwed up or so that its two terminal smooth cylindrical portions can slide. The said stem also has a cavity 21 which can be closed by plug 26 to form a chamber communicating with the outside atmosphere through an air intake fitted with an antibacterial filter 39 consisting of an aperture 28 coaxial with the longitudinal axis of said plug 26 and four apertures 24 made in the base of cavity 21.

Container 22 of the liquid component of the bone cement is housed within cavity 21, which is provided internally with means for breaking container 22.

In the embodiment illustrated in FIGS. 1 to 5, container 22 is in the form of a glass vial, while the means for breaking the container comprise a cylinder 23. This cylinder 23 has a through cylindrical aperture 34 with a longitudinal axis which converges with the longitudinal axis of the cylinder towards the base. The said cylinder acts together with plug 26, which is movable in an axial direction with respect to stem 20. In order to break the glass vial all that is necessary is to press plug 26 downwards so that it in turn presses the base of the vial downwards, forcing the lower spindle-shaped extremity of the vial to slide along the inner wall of said aperture 34.

Because aperture 34 is not coaxial with the longitudinal axis of the vial, the spindle-shaped end of the vial is forced to move laterally. In this way the axial pressure on plug 26 is converted into a bending moment applied to the base of the collar of the vial, in a previously weakened annular area 33.

Cylinder 23 is provided at each end with four radial channels 36 at 90° intervals connected in pairs for four channels 36' located on the lateral surface of the cylinder and running parallel to the longitudinal axis thereof. The said channels have the function of assisting passage of the liquid from the zone above cylinder 23 to the zone below it when the vial breaks.

Chamber 14, which forms the aseptic container for the powder component of the bone cement, and chamber 21 within the stem of plunger 13 are placed in mutual communication by means of four apertures on holes 24 located on the head 25 of the said plunger. These holes are protected by a filter 27 housed in the base of the cavity in the said plunger so as to prevent fragments of glass passing from chamber 21 within the stem of the plunger into the chamber beneath which the powder component of the cement is contained.

The stages required in order to obtain a cement paste which is ready to be directly emplaced by the apparatus to which the invention relates will now be illustrated.

The person preparing the cement for the surgeon initially removes a device which is sterile in all its parts, already arranged as illustrated for example in FIG. 2, from an aseptic container. In this embodiment of the apparatus according to the invention, container 22 of the liquid cement component consists of a substantially cylindrical glass vial with a slightly concave end 22' and another end elongated outwardly to form a point 22". Close to the base of point 22" there is provided a zone 33 of annular weakening, so that the vial will break in a predetermined manner.

The device for breaking the vial consists of a cylinder 23 of the type illustrated above, located at the base of cavity 21 in the stem of plunger 13, separated from the head 25 of the plunger by a protective filter 27.

The vial is inserted in cavity 21 with its end 22' upwards, and point 22" inserted in hole 34 of cylinder 23. Plug 26 is in a raised position with respect to contact plane 35 within stem 20, but pressure is gently applied to the top 22' of the vial so that the pressure exerted on plug 26 in a downward direction causes a bending moment to be produced in the base of point 22" of the said vial.

The stem of plunger 13 is inserted in hole 18 of cover 12 with the lower end of the threaded portion just engaging the thread in said hole 18. In this way, head 25 of the plunger together with cavity 14 in body 11 bounds a chamber which acts as a container for the powder component of the cement.

At the lower end of body 11, a plug 17 is screwed onto needle 16 which projects from the body itself.

Internally, extending from its base, this plug has a cylindrical projection 17' of diameter corresponding to the internal diameter of said needle 16, so as to prevent firstly the powder component and then the paste contained in body 11 from obstructing needle 16. Within plug 17, at its base, there is provided a seal 32 which ensures that the plug remains tight when it is screwed down onto needle 16.

Figure 3:
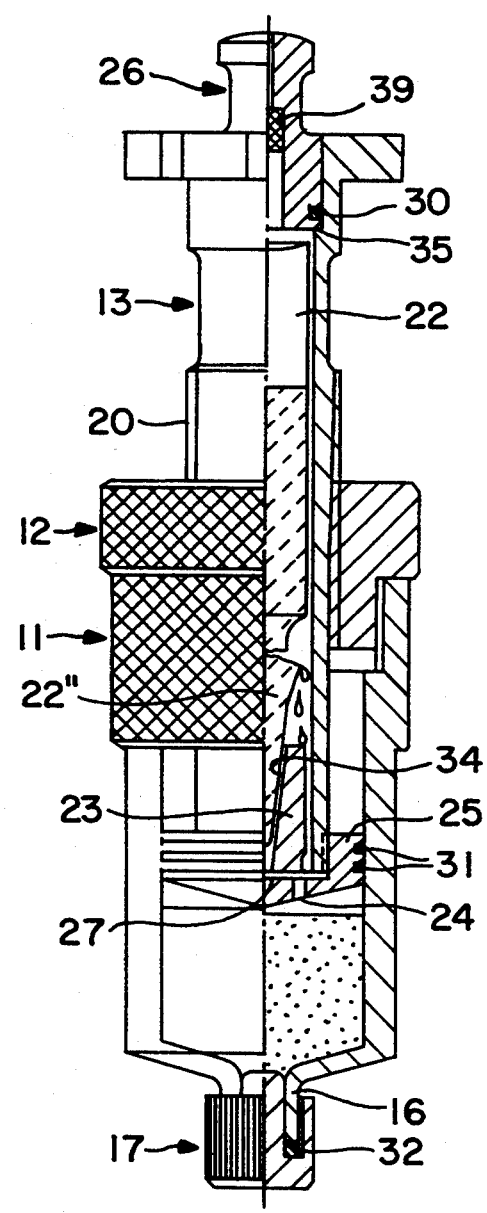
FIG. 3 is a view impartial cross-section of the apparatus of FIG. 1 during the stage immediately following breakage of the vial.
Figure 4:
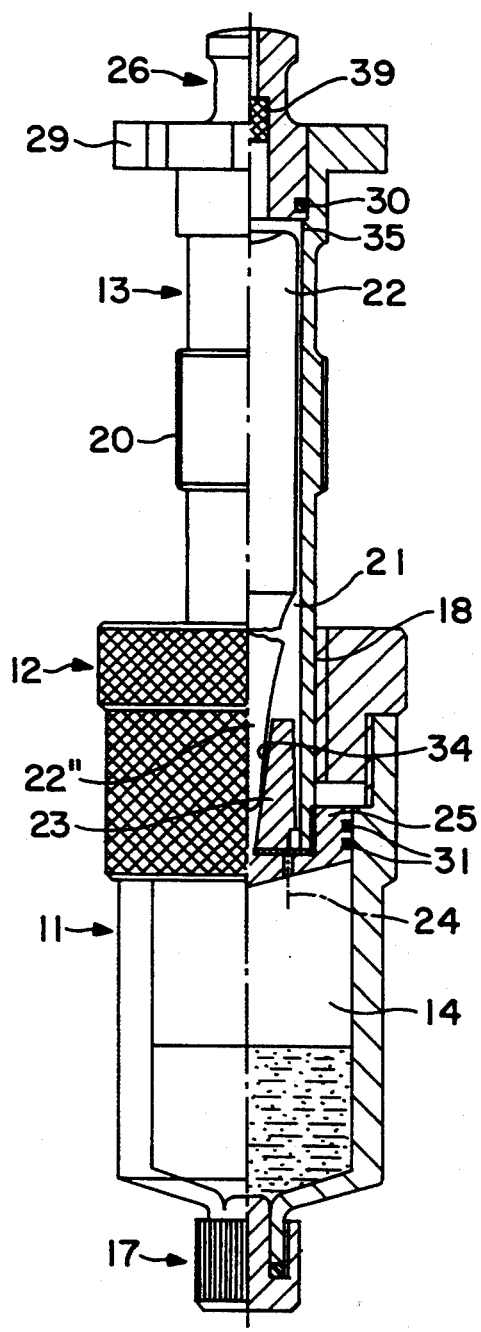
FIG. 4 is a view in partial cross-section of the apparatus of FIG. 1 during the stage in which a negative pressure is created therewithin.

With means arranged as illustrated, the operator begins the stage of preparing the bone cement paste, by first exerting a pressure downwards on the top of plug 26. As a result of such pressure, plug 26 pushes the vial downwards, and this, being constrained to slide with point 22" in hole 34 of cylinder 23, breaks through by bending in predetermined zone 33. As illustrated in Fig. 3, following this breakage, the liquid component begins to fall by gravity, first through hole 34 and channels 36, and then filter 27 and holes 24, coming into contact with the powder present in the underlying chamber. The time necessary for falling by gravity alone would however be too long so the operator draws plunger 13 upwards, as illustrated in FIG. 4, thus setting up a negative pressure in the chamber containing the powder component so that liquid is sucked into the said chamber very quickly. The operator then shakes the entire device repeatedly in order to assist the reaction between the two components and to obtain a more homogeneous paste.

The operator then orientates the device so that plug 17 is at the top, and then removes the said plug and screws a threaded connection 37 onto needle 16 of body 11 in order to attach a flexible cannula 38 of such a length that it reaches the anatomical sites involved in the operation when the paste is emplaced. Holding the device with cannula 38 pointing upwards he pushes the plunger upwards to that most of the air contained within the device is expelled.

Figure 5:
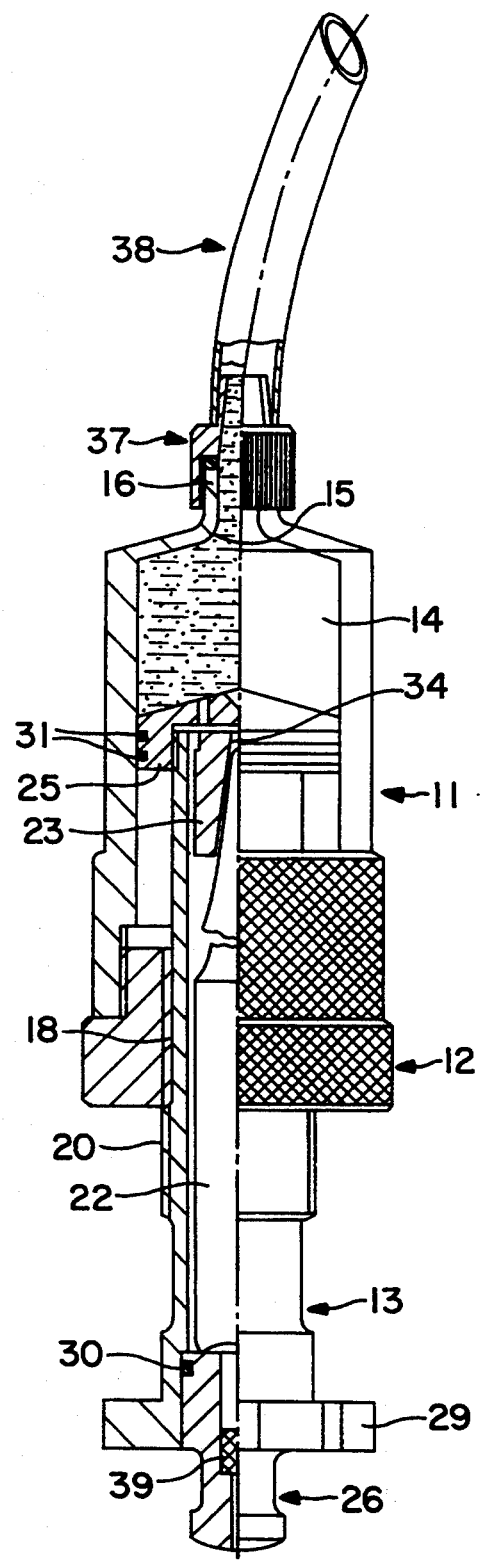
FIG. 5 is a view in partial cross-section of the apparatus of FIG. 1 ready for delivery of the cement contained therein.

At this point the operator, with the device positioned as shown in FIG. 5, is ready to deliver a perfectly aseptic bone cement, which is not stratified and which has minimum porosity, directly in situ. In fact, extrusion through needle 16 produces greater compactness in the paste, reducing the bubbles produced by air and the vapours of the liquid component by compression.

It is clear that in cases where the area into which the cement has to be extruded is easily accessible, extrusion is performed without fitting cannula 38.

Threading of the central portion of the stem 20 of plunger 13 takes place during the extrusion stage, and this, when engaged with the thread in hole 18 of cover 12, makes it possible for the cement paste to be extruded with ease and without excessive effort, despite its high viscosity.

Although not illustrated in the drawings, paste extrusion may be mechanical instead of manual, effected through an external device, for example a rack, which by connecting body 11 or cover 12 to the plunger, moves the latter longitudinally, in order to reduce effort by the operator. This plunger may also be moved by a pneumatic device externally connecting body 11 or cover 12 to the plunger itself. It is clear that the device must be modified in such cases, eliminating the central threaded portion of stem 20 of plunger 13 so that this can move freely within hole 34, which is also not threaded, of cover 12.

Although not illustrated in the drawings, a connection valve for connection to a vacuum unit may be fitted to the base of body 11 close to needle 16 so as to achieve greater removal of air and therefore less porosity in the cement.

From what has been described above, it will be clear that at no time during the stages in the preparation of the cement paste can the operator inhale harmful vapours of the liquid component of the cement, given that these always remain within the internal chambers of the device itself during all the various stages.

Figure 6:
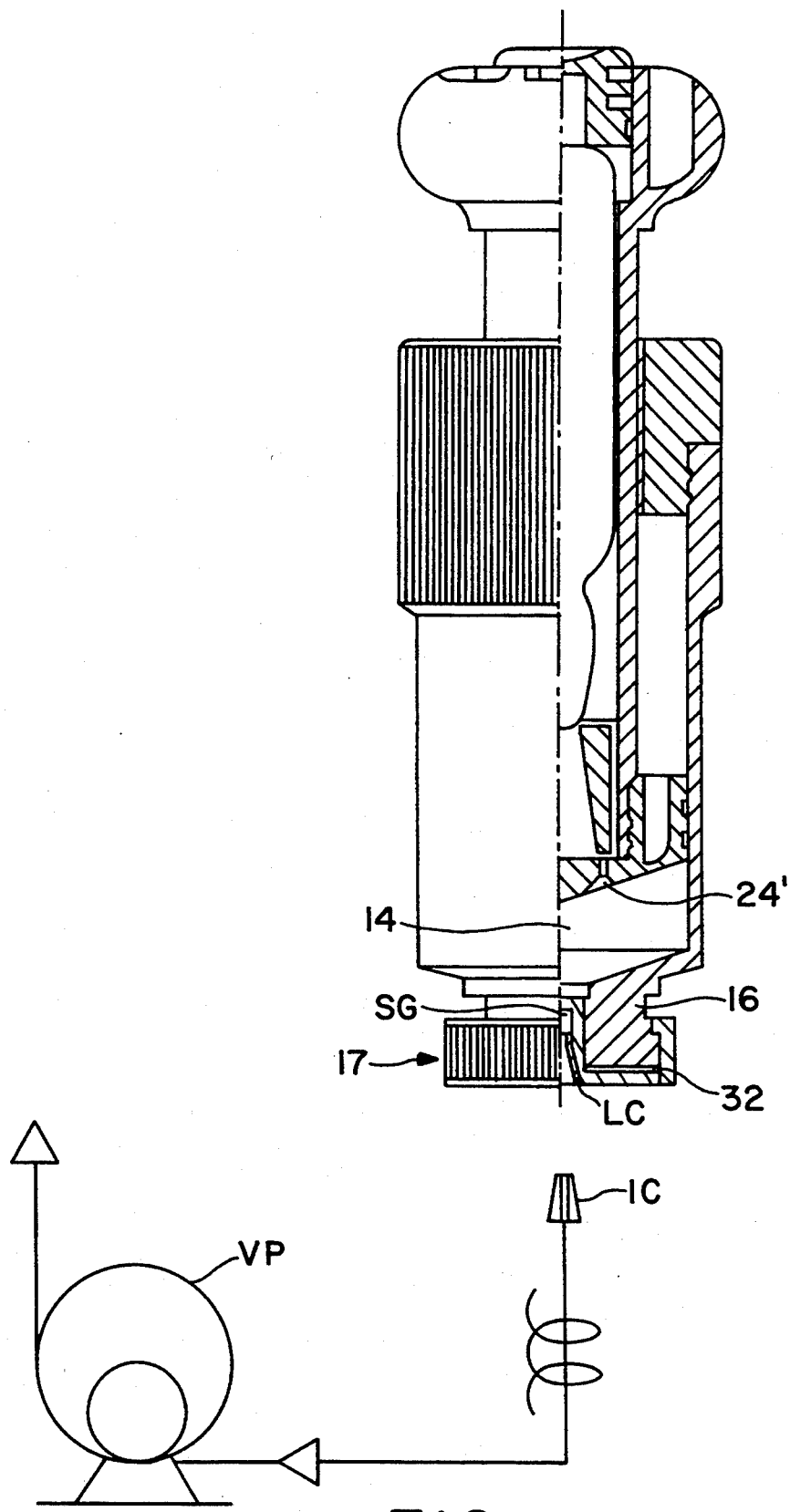
FIG. 6 is an imploded view in partial cross-section of a second embodiment of apparatus according to the invention.

FIG. 6 illustrates a second embodiment of the invention which differs from the first in some aspects relating to shape, which improve the handleability of the device, such as the shape of the grip 29 for plunger 13, the shape of plug 26, which now only projects minimally from the grip, the shape of head 25 of the plunger itself, which is now provided with holes 24' which are hollowed out at the lower end in order to aid the outflow of liquid from chamber 21, and the external knurling on cover 12 and part of body 11. Also the two embodiments differ in the manner in which the various constituent parts of the device are connected together.

In the second embodiment of the invention, cover 12 is in fact attached to body 11, the former being partly inserted into the latter under pressure, while plug 17, instead of being screwed onto needle 16 of body 11, is attached to the said needle by means of a bayonet attachment which is itself known.

The vacuum pump VP can be connected to the plug 17 via an air sucking SD provided with an inlet connection 1C. The plug comprises a (Luer cone) pipe union LC designed to receive the inlet connection 1C, and a sealing gasket SG.

Figure 7:
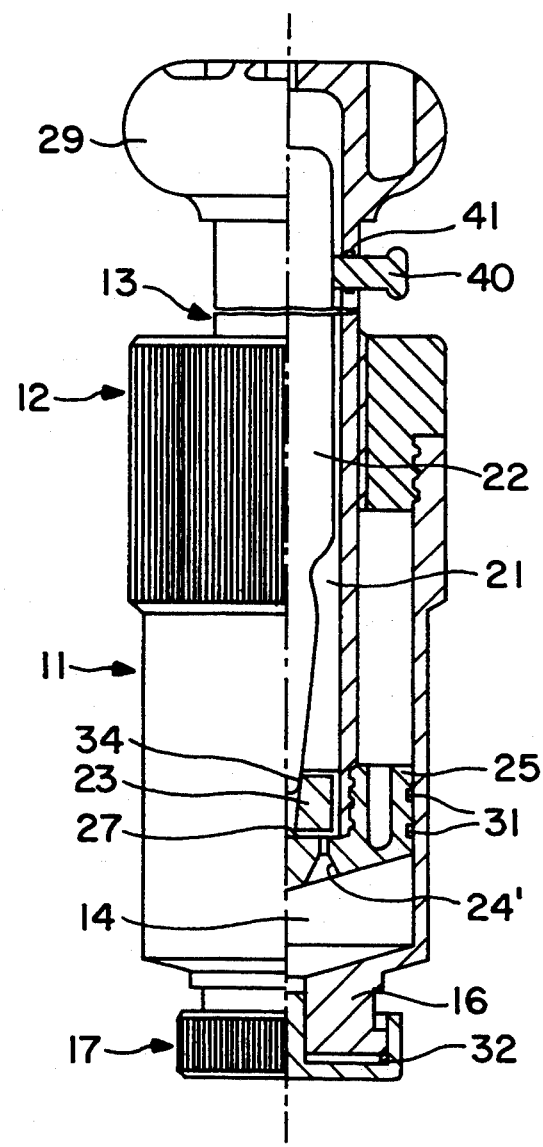
FIG. 7 is a view similar to that in FIG. 6 of a third embodiment of the invention.

Integers:

Vacuum pump VP
sucking duct SD
inlet connection 1C
Luer cone pipe union LC
sealing gasket SG FIG. 7 illustrates an alternative embodiment of the apparatus according to the invention, in which the bending moment which causes breakage of the glass vial containing the liquid component is achieved by cylinder 23 acting in concert with a push button 40 which projects into cavity 12 of plunger 13 and can be displaced from the outside in a direction perpendicular to the longitudinal axis of the said vial. While cylinder 23 has the function of jamming the point of the vial against hole 34, push button 40 can be used to displace the vial laterally and thus to produce the bending moment necessary for breakage of the vial. This push button, which is located on the lateral wall of plunger 13 close to grip 29 of the plunger itself, is provided with a seal 41 which prevents external air from entering into stem 20 and escape of the toxic vapours of the liquid component.

Figure 8:
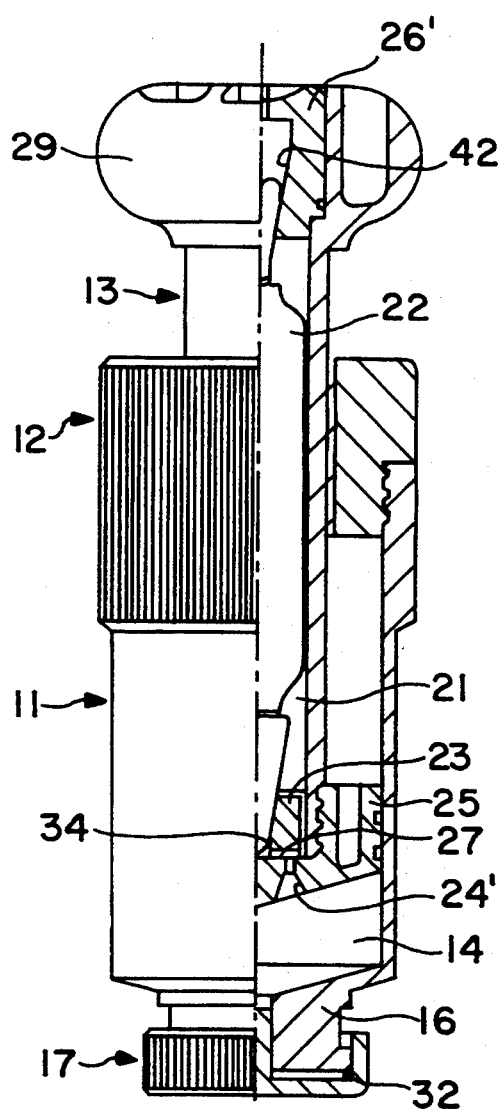
FIG. 8 is a view similar to that in FIG. 6 of a fourth embodiment of the invention.

A fourth embodiment of the apparatus according to the invention illustrated in FIG. 8, provides for the use of containers 22 for the liquid component consisting of a substantially cylindrical glass vial fitted with two longitudinally outwardly elongated points of the type described above. The means for breakage of the said vial consists of a cylinder 23, already illustrated, which acts together with plug 26'. This plug can be displaced from the exterior in a longitudinal direction and has at its lower end a cylindrical hole 42 which is offset with respect to the longitudinal axis of plug 26', in the same way as hole 34 of said cylinder 23.

When plug 26' is pushed downwards both the points are stressed by a bending moment which breaks the vial at two predetermined points.

Figure 9:
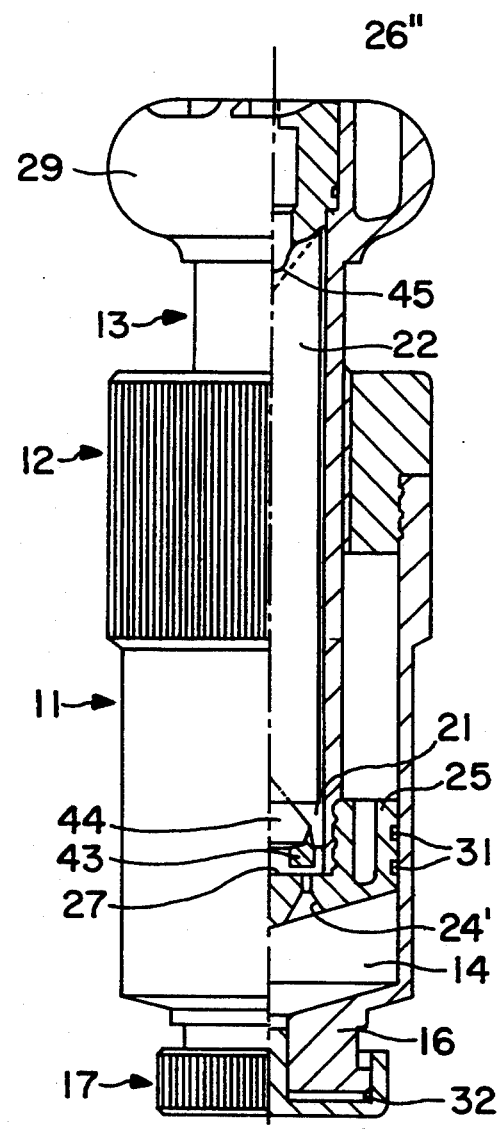
FIG. 9 is a view similar to that in FIG. 6 of a fifth embodiment of the invention.
Figure 10:
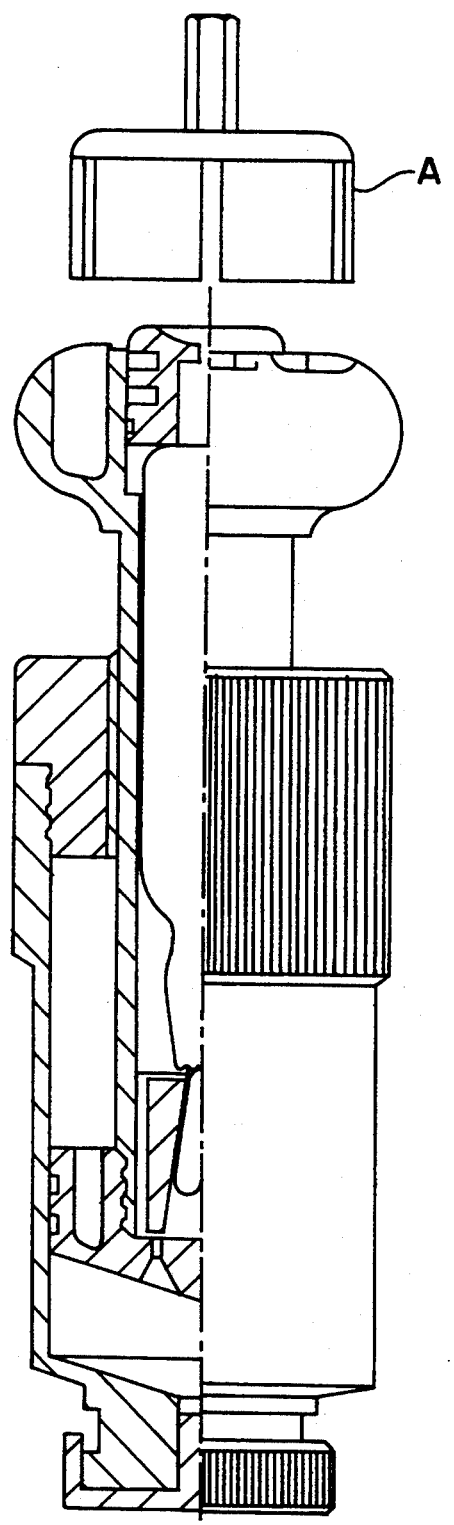
FIG. 10 is a partial cross section of an apparatus according to the invention including rotating mechanical means in the form of a coupling head A arranged to be operatively connected to a locking chuck for extruding the cement past.
Figure 11B:
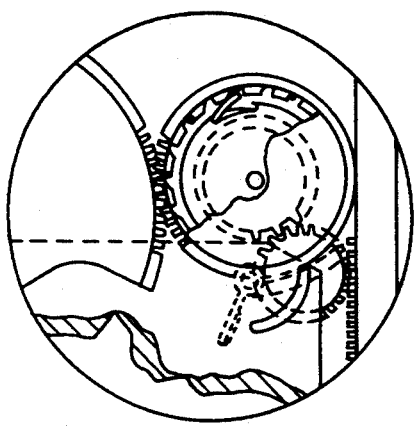
FIG. 11 is a partial cross section of an apparatus according to the invention provided with rack and pinion mechanical means including handles which can be actuated through a ratchet gear, for extruding cement paste.
Figure 11A:
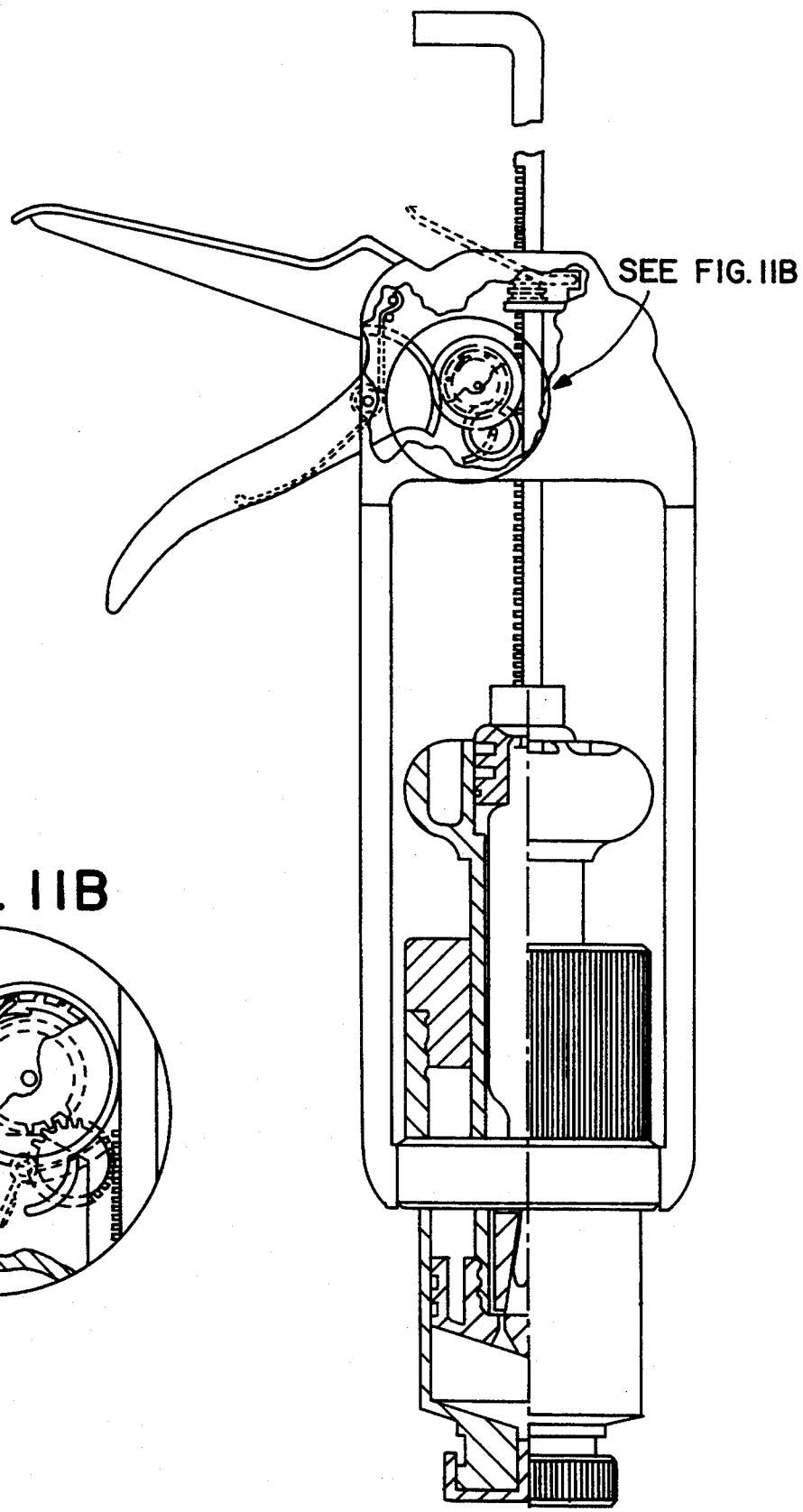
Figure 12:
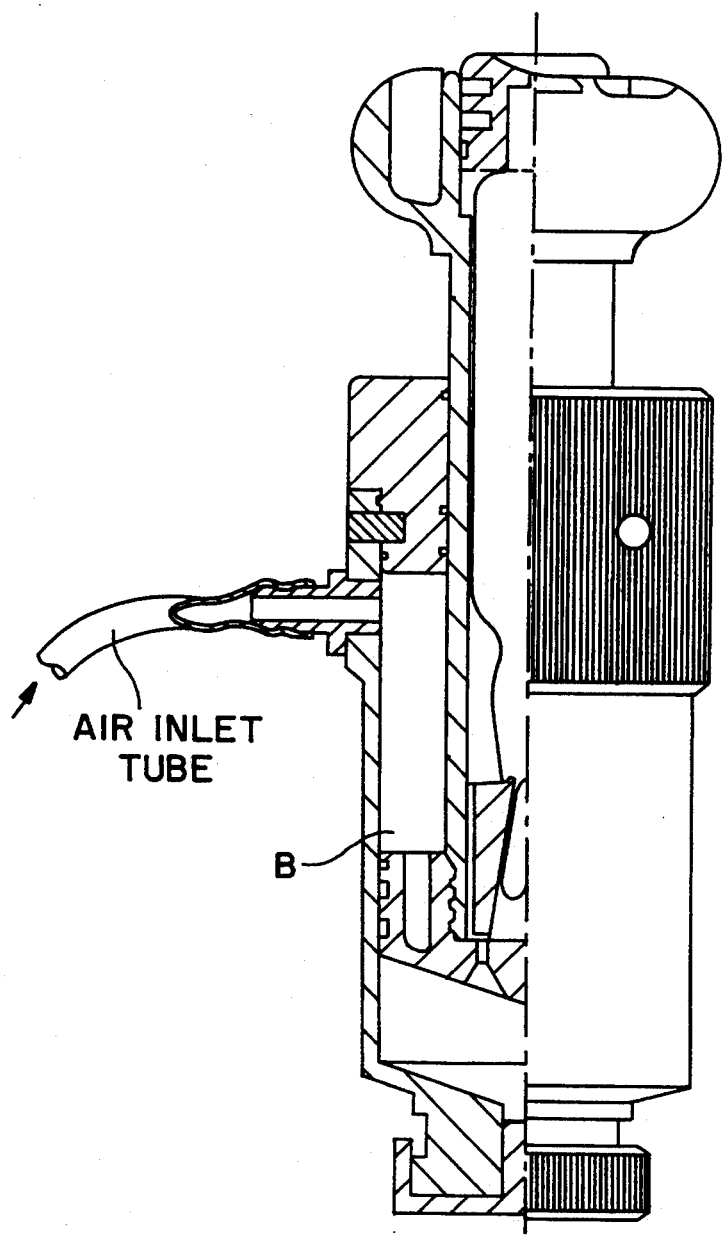
FIG. 12 is a partial cross section of an apparatus according to the invention including a pneumatic device comprising a compressed air inlet tube to a compressed air source and in communication with an annular space.
Figure 13:
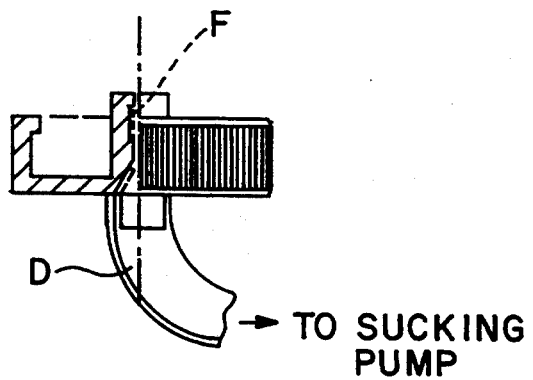
FIG. 13 is a partial cross section of a sealing plug including an inner filter for use in communication with a sucking pump via an air sucking duct.

A fifth embodiment of this means according to the invention illustrated in FIG. 9, provides for the use of containers 22 for the liquid component consisting of a cylinder of metal or plastics material internally coated with a material which does not react with the liquid contained. The device for breaking the container consist of cylinder 43 of diameter corresponding to the diameter of the cavity in the stem of plunger 13, located at the base of cavity 21 behind filter 27 and provided with an upwardly facing cutting point 44 which is capable of perforating the lower end of the said cylinder, and by plug 26" of chamber 21, which has a second downwardly facing point 45 alongside cavity 21 which perforates the upper end of the said cylinder. Breakage of both the ends of container 22 takes place through the joint action of said cylinder 43 and plug 26" when the plug is pushed against the said container in a longitudinal direction from the exterior.

As a result of breakage of both the ends of the container of liquid component the latter falls more quickly through gravity.

Although not illustrated in the drawings, container 22 for the liquid component may consist of an envelope of plastics material internally coated with a material which does not react with the liquid component. In this case, the envelope which is provided with two rigid cylindrical units at its ends is housed in cavity 21 of plunger 13. The first of these cylindrical ends is located on the base of cavity 21 where suitable guides prevent this from rotating with respect to the plunger itself. The second cylindrical member consists of said plug 26, which by projecting from grip 29 enables the operator to rotate it by an amount sufficient to break the envelope through torsion.

What is claimed is:

1. A process for mixing a bone cement formed from two components, one liquid and one powder, the components being separate until the cement is required for use, each component comprising a mixture of mutually compatible components, the process comprising:
    separately storing the liquid and powder components to be mixed within a container having a plurality of chambers aseptically isolated from atmosphere;
    opening the container for the liquid component located within one of the chambers;
    creating a negative pressure in the chamber containing the powder component, the negative pressure causing suction of the liquid component into the chamber containing the powder component, the two chambers being kept isolated from outside atmosphere;
    mixing the two components by agitation of the container;
    compacting the bone cement obtained by compression; and
    extruding the cement for direct in situ emplacement of the cement.

2. The process as claimed in claim 1 further comprising the step of inserting a flexible cannula to direct the outflow of the cement.

3. A process as claimed in claim 1 wherein the cement is extruded by manual action.

4. A process as claimed in claim 1 wherein the cement is extruded by mechanical action.

5. A process as claimed in claim 1 wherein the cement is extruded by pneumatic action.

6. A process as claimed in claim 1 wherein compacting the cement is accompanied by further aspiration of air by means of vacuum generating equipment.

7. Apparatus for holding and mixing cement components comprising:
    a body having a longitudinal axis, a base and a hollow cylindrical needle projecting outwardly from the base;
    a cover attachable to the body, the cover having an aperture which is coaxial with the longitudinal axis of the body;
    a plunger capable of reciprocable axial movement in the aperture and the body, the plunger having a stem and a head which, with the body, defines a chamber for a aseptically housing a powder component of the cement, the plunger further having a cavity therein for housing a container containing a liquid component of the cement;
    a sealing plug for attachment to the needle;
    means for breaking the container when located in the cavity;
    a plurality of holes between the cavity and the chamber to permit the powder component and the liquid component to be placed in mutual communication after the container has been broken; and
    a filter located on the head of the plunger.

8. Apparatus as claimed in claim 7 wherein:
    the plunger is a substantially cylindrical and hollow stem with an enlarged upper end forming a grip;
    the head is attached at one end of the stem by attachment means;
    a seal is located in a circular channel in the head and seals against an inner wall of the body;

the plug can be partly inserted at an end of the cavity remote from the head and includes air intake means and antibacterial filter protecting such intake means;

the stem has an outer surface having a central threaded portion between two smooth cylindrical portions; and the stem is axially movable within the aperture of the cover so that the threaded portion thereof can be threadedly engaged or the smooth portions thereof can slide.

9. Apparatus as claimed in claim 7 wherein the stem has an outer lateral surface which is entirely cylindrical and smooth, the stem being slidably axially movable in the aperture of the cover.

10. Apparatus as claimed in claim 9 wherein the plunger is moved by a mechanical device.

11. Apparatus as claimed in claim 9 wherein the plunger is moved by a pneumatic device.

12. Apparatus as claimed in claim 7 wherein:

the container for the liquid component comprises a substantially cylindrical glass vial having one blunt end and an elongated point at another end thereof, the point being in the proximity of the base, the vial further comprising an annular zone of weakness; and the means for breaking the vial comprises a cylinder having a diameter substantially the same as that of the cavity and a height less than that of the point of the glass vial, the cylinder having a through hole, the point having a longitudinal axis which is inclined relative to a longitudinal axis of the cylinder, said longitudinal axes of the point and cylinder intersecting near an upper end of the cylinder, whereby when the plug is displaced inwardly in a longitudinal direction, a bending moment is applied to the point of the vial to break it at the zone of weakness.

13. Apparatus as claimed in claim 12 wherein the cylinder is provided with four radial channels at each of its ends spaced at substantially 90° from each other, the four radial channels being connected in pairs to four longitudinal channels located on an outer surface of the cylinder and parallel to the longitudinal axis thereof.

14. Apparatus as claimed in claim 7 wherein:

the container of the liquid component comprises a substantially cylindrical glass vial having two ends which are elongated to form a point;

the means for breaking acts on the two ends of the vial and comprises a cylinder located near the base of the cavity and the plug which can be inwardly displaced in a longitudinal direction, the plug including a cylindrical hole having a longitudinal axis which is inclined relative to a longitudinal axis of the plug, the longitudinal axes of the cylindrical hole and the plug intersecting near a lower end of the plug.

15. Apparatus as claimed in claim 14 wherein the means for breaking the vial further comprises a push button projecting into the cavity of the plunger, the push button being displaceable from outside the apparatus in a direction perpendicular to the longitudinal axis of the vial, the push button being located in an upper portion of the stem and within a hole thereof, said hole being provided with a seal.

16. Apparatus as claimed in claim 14 wherein the cylinder is provided with four radial channels at each of its ends spaced at substantially 90° from each other, the four radial channels being connected in pairs to four longitudinal channels located on an outer surface of the cylinder and parallel to the longitudinal axis thereof.

17. Apparatus as claimed in claim 7 wherein:

the container for the liquid component comprises a cylinder made of materials selected-from the group comprising metals and plastics, the container being internally coated with a material which does not react with the liquid component;

the means for breaking the container comprises a cylinder having a diameter corresponding to that of the cavity in the stem, the cylinder being provided with a first point adapted to pierce a lower end of the container, the plug of the chamber including a second point adapted to pierce an upper end of the container, whereby the upper and lower ends of the container are broken through joint action of the cylinder and plug when the plug is pushed against the container in a longitudinal direction.

18. Apparatus as claimed in claim 17 wherein the cylinder is provided with four radial channels at each of its ends spaced at substantially 90° from each other, the four radial channels being connected in pairs to four longitudinal channels located on an outer surface of the cylinder and parallel to the longitudinal axis thereof.

* * * * *